United States Patent [19]

Couderc

[11] 4,426,160

[45] Jan. 17, 1984

[54] DEVICE FOR MEASURING THE DEFORMATION OF A MATERIAL UNDER THE INFLUENCE OF HEAT AND ITS APPLICATION TO THE DETERMINATION OF THE WETTING POWER OF PITCHES

[75] Inventor: Pierre Couderc, Bethune, France

[73] Assignee: Huiles, Goudrons et Derives, Paris la Defense, France

[21] Appl. No.: 335,439

[22] Filed: Dec. 29, 1981

[30] Foreign Application Priority Data

Dec. 30, 1980 [FR] France ................................. 80 27742

[51] Int. Cl.³ ............................................ G01N 25/04
[52] U.S. Cl. ........................................ 374/45; 374/55
[58] Field of Search ....................... 374/45, 46, 51, 57, 374/55, 56, 4, 19, 22, 16; 356/36, 72

[56] References Cited

U.S. PATENT DOCUMENTS

| | | | |
|---|---|---|---|
| 1,184,837 | 5/1916 | Edgecomb | 374/22 |
| 3,077,764 | 2/1963 | Kapff | 374/19 |
| 3,587,293 | 6/1971 | Bowers | 374/16 |
| 4,083,224 | 4/1978 | Gayst | 374/19 |

*Primary Examiner*—Charles E. Frankfort
*Assistant Examiner*—David R. Schuster
*Attorney, Agent, or Firm*—Millen & White

[57] ABSTRACT

A method and apparatus for optically making physical measurements of materials which deform upon application of heat thereto. The device comprises a source of light, an at least partly transparent chamber having a heating source which can be programmed to operate as a function of time, and with a porous support designed to support a deformable material within the chamber. A photo-electric receiver 5 and an optical lens 7 are also provided for imaging of the material during deformation on the photo-electric receiver. In order to perform the imaging, the source of light, the porous support, the photo-electric receiver and the optical lens 7 are optically aligned. In a specific application, the apparatus can be used to determine the wetting power of pitches.

15 Claims, 5 Drawing Figures

DEVICE FOR MEASURING THE DEFORMATION OF A MATERIAL UNDER THE INFLUENCE OF HEAT AND ITS APPLICATION TO THE DETERMINATION OF THE WETTING POWER OF PITCHES

BACKGROUND OF THE INVENTION

This invention relates to an apparatus for measuring the deformation of a material under the influence of heat, and to a method of use of the apparatus for determining the wetting power of materials which deform under the influence of heat. More particularly, the invention has special application for measuring the deformation of pitches under the influence of heat and for determining the wetting power thereof.

These are prior art methods known for measuring the temperature at which a material, when heated, passes from the solid state to the viscous state and then to the liquid state. By these methods, the ball and ring softening point or the Durran melting point, or the Kraemer-Sarnow (KS) softening point can be determined for thermoplastic materials. However, the prior art methods do not provide information on the behavior of the materials throughout the entire interval during which they are heated.

It is often useful and necessary to know the nature of the change in the shape of a material being heated, and particularly, the changes occuring in the material in relation to a porous support, with which it is combined, and which support is not very sensitive to the action of heat, i.e., does not undergo significant structural changes. In the particular field of use of pitch binders for electrodes, it is useful to know the wetting power of the pitch because it provides an estimate of the utility of the pitch in the manufacture of electrodes. It should be noted at this point that by the term "pitches" is meant black or dark-brown solid cementitious materials which gradually liquify when heated and which are generally obtained as residua in the partial evaporation or fractional distillation of tar. Furthermore, by the term "wetting power" is meant the ability of the material, e.g., pitches, to wet or penetrate into the pores of the support upon which it is being liquified. More specifically, it is the ability of the material to be respectively adsorbed and absorbed on a porous support. In particular, it is useful to know the temperature, at which a pitch is completely absorbed in a coke support. In addition, it is useful to know how this absorption occurs, i.e., how the molten pitch penetrates the pores of the coke support. It is also appropriate to point out that by the term "coke" is generally meant a bituminous coal material from which the volatile constituents have been driven off by heat. The type of "coke" formed varies depending on temperature, position or the particles of coal from which it is formed, and although commonly artificially made can occur naturally and will generally be porous.

SUMMARY OF THE INVENTION

It is thus an object of the invention to provide a device for measuring the deformation of a material under the influence of heat.

It is another object of the invention to provide a device for measuring the deformation of pitches under the influence of heat and to determine the wetting power thereof.

It is still another object of the invention to provide a method for measuring the deformation of a material under the influence of heat, and more particularly, to measure the deformation of pitches to determine the wetting power thereof.

It is yet still another object of the invention to provide a method of selecting pitches for use in manufacturing of electrodes according to the measured wetting power thereof.

Upon further study of the specification and appended claims, further objects and advantages of this invention will become apparent to those skilled in the art.

In accordance with the invention, a device is provided for measuring the deformation of a material under influence of heat. The device generally comprises a source of light, an at least partly transparent chamber for allowing light to travel therethrough equipped with a heating device which can be programmed to operate as a function of time, and having a porous support in the chamber designed to receive the material thereon, a photo-electric receiver, and an optical lens for enabling an image of the material to be formed on the photo-electric receiver. In the device of the invention, the source of light, the porous support, the photo-electric receiver and the optical lens are optically aligned with the porous support located between the light source, and the lens and receiver.

In a further embodiment it is convenient to insert a diaphragm and/or an optical lens between the source of light and the chamber for creating a beam of parallel light rays from the light source. The porous support can rest on a base, which either rests on the bottom of the chamber or can be suspended from the top of the chamber. The material upon which measurements are performed is solid at ambient temperature. Advantageously the material is shaped, preferably like a cylinder, or as a parallelepiped.

The nature of the light source employed depends on the particular type of photo-electric receiver used. More specifically, if the photo-electric receiver comprises a photomultiplier tube, provided with a vertical slit on which the image of the material 6, produced by the lens 7, is focused, it is necessary that the light source have constant intensity and that the light emitted have a wave-length compatible with the operational characteristics of the photomultiplier tube. In this case, it will therefore be possible to use a conventional light source, i.e., a filament lamp supplied with a stable voltage i.e., non-fluctuating voltage, or alternatively, the light source can comprise a laser source. These elements are generally conventional in nature and will not be elaborated on in greater detail.

If the photo-electric receiver comprises an array of microphotodiodes arranged in the form of a vertical bar, the light source need not have a constant intensity nor need it be monochromatic because the microphotodiodes will then operate on the "all or nothing" principle, as will be clarified below. It is necessary, however, in this case that the intensity of light emitted by the source be sufficient for saturating the microphotodiodes. By the term "all or nothing" it is intended that each of the microphotodiodes in the array will have an output of a fixed value once a minimum intensity of light strikes it, and the output will not vary in accordance with increased or decreased (but not lower than the minimum intensity) intensity of light striking the microphotodiodes. The output will be zero when an opaque sample will intercept the light beam.

As previously discussed, the chamber has to be at least partly transparent in a manner so as to allow transmission of the light beam originating from the source therethrough. The chamber may be completely transparent and comprise for example, a glass cylinder, the axis of which is at right angles to the light beam, and also at right angles to a plane defined by the top surface of the porous support in the chamber. The chamber may also alternatively be partly transparent and comprise for example, a hollow structure in the shape of a parallelepiped with the two walls parallel to the light beam being opaque, and the two walls at right angles to the light beam being transparent. The transparent walls of the chamber which are thus located spaced opposite each other, are preferably made of a material that is not deformable by heat. For instance, the walls may be made of glass, for example Pyrex grade glass.

Alternatively, the light source can be situated inside or outside the chamber. If it is situated inside the chamber, the chamber need be only transparent on one side for the passage of the light beam to the photo-electric receiver.

BRIEF DESCRIPTION OF THE DRAWINGS

Various other objects, features and attendant advantages of the present invention will be more fully appreciated as the same becomes better understood when considered inconjunction with the accompanying drawings, in which like reference characters designate the same or similar parts throughout the several views, and wherein.

DETAILED DISCUSSION OF THE INVENTION

Figure 1:
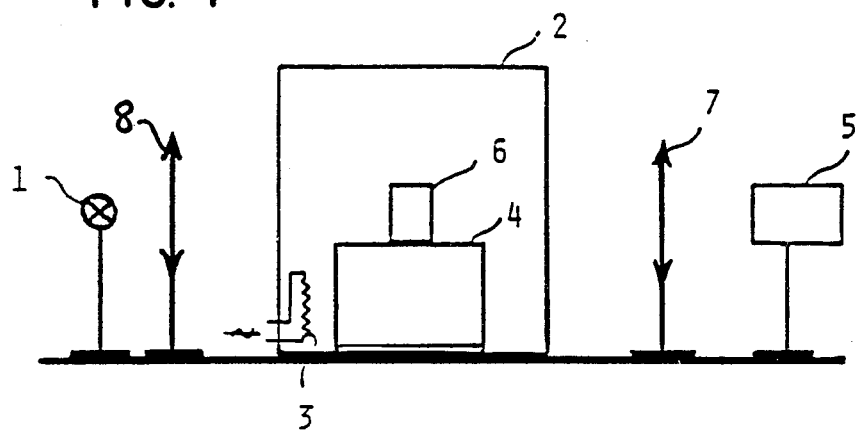
FIG. 1 is a schematic diagram of the device of the invention showing the support and material to be tested located within the chamber.

According to one embodiment of the invention as shown in FIG. 1, the light source 1, a porous support 4, a photo-electric receiver 5 and an optical lens 7 are both optically and linearly aligned. Alternatively these elements need not be linearly aligned, however, in this case the device will then require in addition, a reflective element, situated in the path of the light beam originating from the source 1, before or after its screening by the material 6 to ensure that the beam intercepted by the material 6 on the porous support and is directed to the photo-electric receiver 5. The reflective element can be a mirror or a total reflective prism, situated, for example, inside the chamber and will be conventional in nature. The device may further comprise an optical lens 8 inserted between the source of light 1 and the chamber 2.

The porous support 4, will generally have a porosity of between 0.1 and 0.9,—ratio of pore volume to total volume, preferably 0.2 to 0.7, and more preferably 0.3 to 0.5. Furthermore, the porous support will be, for example, a powder bed, contained in a boat, or a pellet of sintered material. The powder, contained in a boat, has, for example, a particle size distribution of between 10 and 1000 $\mu m$, preferably 20 to 200 $\mu m$, and more preferably 40 to 70 $\mu m$. The pellet of sintered material has, for example, a pore diameter of between 10 and 200 $\mu m$, preferably 20 to 150 $\mu m$, and more preferably 40 to 90 $\mu m$.

Figure 4:
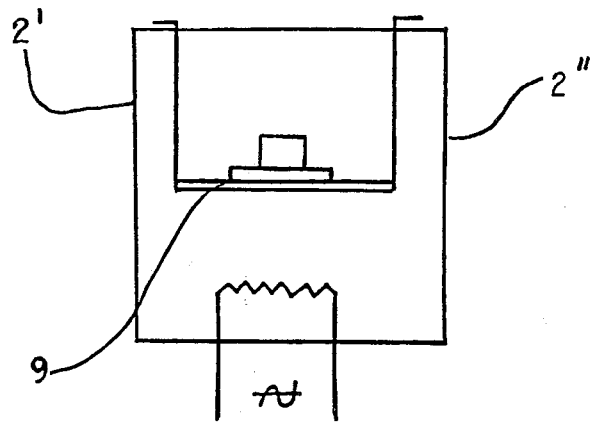
FIG. 4 is a schematic diagram of an alternative embodiment of the chamber of the device with the porous support supported from the top of the chamber.

In FIG. 4 the chamber 2 is shown with transparent walls 2' and 2'' with the porous support supported suspended from the top of the chamber 2 by means of a suspended base 9. This base 9 can, as previously described, merely rest on the bottom of the chamber 2.

Figure 5:
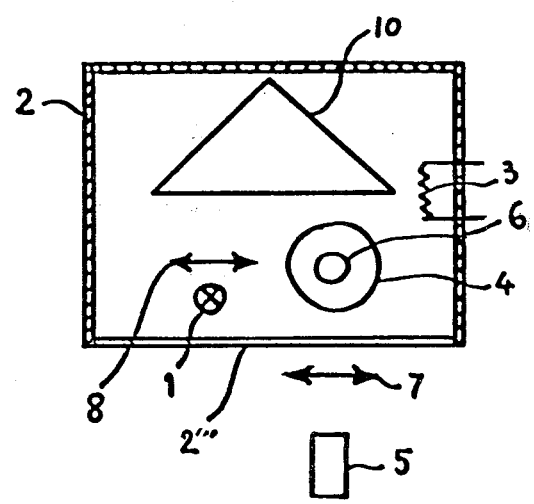
FIG. 5 is a schematic diagram (top view) of an alternative embodiment of the chamber of the device with a total reflection prism used to optically align the source of light, the porous support, the photoelectric receiver and the optical lens.

In FIG. 5 the chamber 2 is shown with only one transparent wall 2''' and with a total reflection prism 10 ensuring the optically alignment of the source of light 1, the porous support 4, the photoelectric receiver 5 and the optical lens 7 which are not linearly aligned. Alternatively the device comprises an optical lens 8 providing from the source 1 a parallel light beam.

The device according to the invention will operate in the following manner. The material 6 is placed on the porous support 4, in the chamber 2 which at that time is at a lower temperature than the temperature at which the material 6 begins to deform. The light source 1 is activated by supporting power thereto, and the optical lens 7 is adjusted so as to form an image of the material 6 on the photo-electric receiver 5. The position of the porous support is checked to ensure that the porous support 4 at least partially intercepts the light beam. In this instance, when the photo-electric receiver 5 comprises a bar of microphotodiodes, a fine adjustment is made on the device, with the aid of a counter, to determine the number of non-illustrated diodes.

The chamber 2 is then heated according to a known equation, $T=f(t)$: wherein, T represents the temperature and (t) the time. At a given temperature, depending on the material, the material 6 begins to deform and the amount of light, received by the photo-electric receiver 5, increases in proportion to the lowering of the height h of the material 6 as it deforms on the porous support 4. The photo-electric receiver 5 then emits a voltage proportional to this lowering of the height, i.e., an increase in light is perceived. This voltage is converted by means of a recorder, into a graphical representation, i.e., a curve on a graph corresponding to $h=(f(t)$,—for a predetermined heating law or, if the recorder is coupled to the temperature programmer of the chamber, to a curve corresponding to $h=f(T)$.

In a refinement of the device, the contour of the material 6 in the course of deformation can be traced at any moment in time. To accomplish this, the photo-electric receiver 5 is mounted so as to be transversely movable with respect to the light beam and is thus capable at any instant in time to scan the zone, on which the image of the material 6 is formed. The means for scanning is conventional as will be evident to one skilled in the art.

The scanning movement has to be sufficiently rapid to enable an almost instantaneous imaging of the contours of the material 6 in the course of deformation at a given temperature. In this embodiment the measurements will supply additional useful information regarding the angle formed between the base of the material 6 and the porous support 4 during deformation, which is a measure of the mutual wettability or non-wettability, as well as the reduction in height (h) of the material as a function of temperature. Thus, a first recorder can be simultaneously used for tracing the changing contour of the sample, and a second recorder for tracing the height (h) of the material as a function of temperature.

The device according to the invention makes it possible to carry out reliable and reproducible measurements, without requiring continuous control by an operator.

Furthermore, the invention is applicable to measure the deformation of any material, which deforms under the influence of heat, such as, e.g., novolac resins such as phenol-formaldehyde resin, pitches and other thermoplastic materials sufficiently opaque to block the passage of light therethrough. The invention is also applicable to the determination of the wetting power of pitches which is a direct function of its deformation over time on a porous support such as coke. In this application, the porous support 4 can be, for example, a bed of coke powder contained in a boat, or a sintered glass pellet. According to the procedure described above, measurement of the deformation is interrupted when the pitch sample has been completely absorbed into the porous support 4 and thus the wetting power can be determined.

Without further elaboration, it is believed that one skilled in the art can, using the preceding description, utilize the present invention to its fullest extent. The following preferred specifie embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

The porous support 4 used was a bed of coke powder, having a particle size distribution of 40–400 micron, with 88% of the particles having a size between 80 and 125 microns, and the deformable materials 6 used were two pitch pellets, having approximately the same physicochemical characteristics, but having different behavior in the manufacture of electrodes. With the pitch No. 2 it is necessary, when manufacturing an electrode, to heat the mixture of pitch and coke at a higher level than with pitch No. 1 to ensure a correct homogenization of the mixture.

Figure 2:
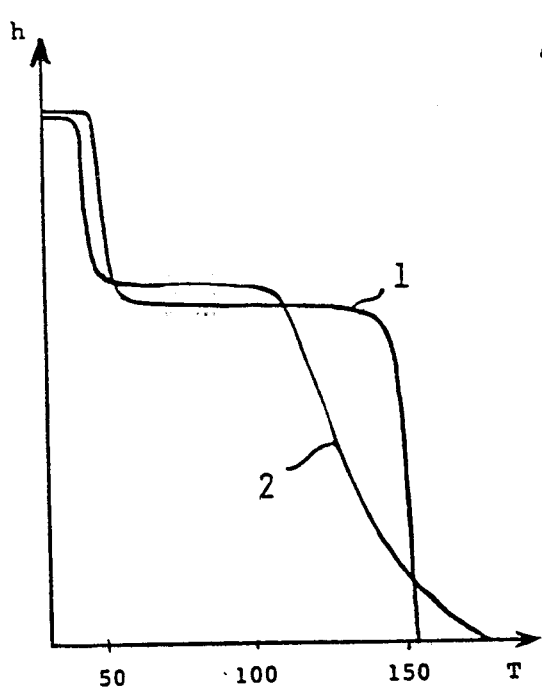
FIG. 2 is a graphical representation comparing the behavior of two different pitch samples heated as a function of temperature.

Of the samples, sample No. 2 has a poor behavior with respect to wetting power relative to sample No. 1. With the aid of the device according to the invention, the curves of FIG. 2 were obtained, showing the height of the pitch pellets as a function of temperature. Thus, it can be observed that the curve, representing pitch sample No. 2, shows a pattern of deformation and absorption on the coke indicating that certain of its components are absorbed with greater difficulty by the bed of coke powder.

EXAMPLE 2

The porous support 4 used was a sintered glass pellet, the pore diameter of which lies between 90 and 150 μm, and the material 6 used was a pellet of phenol-formaldehyde resin of the novolac type, generally obtained by condensation of phenol and formaldehyde in an acid medium. This resin has a Durran softening point of 85° C.

Figure 3:
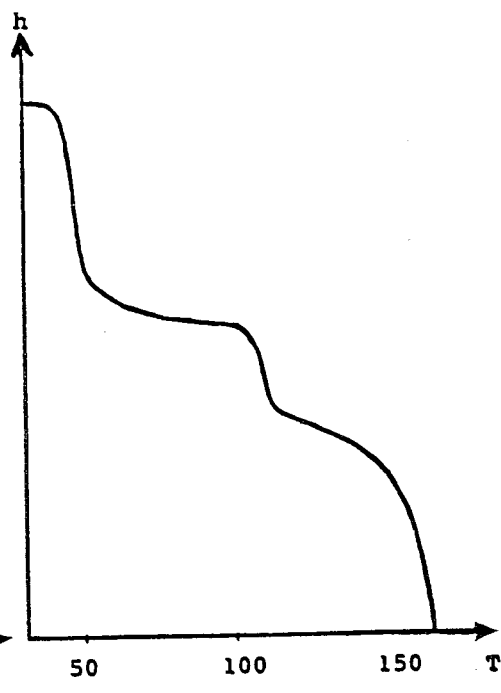
FIG. 3 is a graphical representation of the behavior of a phenol-formaldehyde resin while being heated, and showing absorption of the resin into a porous support as a function of temperature.

FIG. 3 shows the curve, $h=f(T)$, obtained with the aid of the device according to the invention. The first plateau corresponds to the transformation of the resin pellet into a drop, i.e., the melting. The temperature at the center of this plateau corresponds to the melting temperature. The following part of the curve shows the absorption of the sample into the porous support 4.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. An apparatus for measuring deformation of a material under the influence of heat, comprising:
   light source means for providing a beam of light;
   chamber means for receiving a deformable material therein, said chamber means being at least partially transparent for allowing light to pass at least through one wall thereof, and including porous support means for supporting said deformable material thereon, and heating means adapted to operate as a function of time for heating and causing deformation of a deformable material in said chamber means;
   photo-electric receiving means; and
   first optical lens means for forming an image of the deformable material in said chamber means on said photo-electric receiving means, wherein said light source means, porous support means, first optical lens means, and photo-electric receiving means are aligned optically for forming said image on said photo-electric receiving means.

2. An apparatus according to claim 1 further comprising second optical lens means positioned between said light source means and said chamber means for focusing light rays emitted from said light source means to form a beam of parallel light rays.

3. An apparatus according to claim 1 or 2 wherein said light source means is positioned within said chamber means.

4. An apparatus according to claim 1 or 2, wherein said means making up said apparaus are not linearly aligned and further comprising reflective means positioned to be in the path of the light beam in a manner for optically aligning said means making up said apparatus.

5. An apparatus according to claim 1 wherein said photo-electric receiving means comprises a photomultiplier tube.

6. An apparatus according to clain 1 wherein said photo-electric receiving means comprises a bar of microphotodiodes.

7. An apparatus according to claim 6 wherein said microphotodiodes are vertically arranged.

8. An apparatus according to claim 1 wherein said photo-electric receiving means is adapted to be transversely movable with respect to the light beams from the light source means for instantaneously scanning the entire image of the deformable material on the support means.

9. An apparatus according to claim 1 wherein said porous support means comprises a bed of coke powder contained in a boat.

10. An apparatus according to claim 1 wherein said porous support means comprises a sintered glass pellet.

11. An apparatus according to claim 9 wherein said coke powder has a porosity of 0.1–0.9.

12. An apparatus according to claim 10 wherein said sintered glass pellet has a pore diameter of 10–200 μm.

13. An apparatus according to claim 9 wherein said coke powder has a particle size distribution of 10–1000 μm.

14. A method of use of the apparatus of claim 1 comprising providing a pitch as the deformable material on the porous support means for determining the wetting power thereof by heating said pitch within said chamber means for causing deformation thereof.

15. A method of use of the apparatus of claim 1 comprising
heating a pitch material as the deformable material on the porous support means to cause deformation thereof as a function of time and temperature;
transmitting a beam of light in a manner as to be at least partially blocked by said deformable material and porous support means during deformation of the material for forming an optical image on said photo-electric receiving means; and
recording the image transmitted to said photo-electric receiving means of the material undergoing deformation as a function of time and temperature whereby the wetting powder of the material can be determined from said image.

* * * * *